United States Patent
Hart et al.

(10) Patent No.: US 6,827,938 B2
(45) Date of Patent: Dec. 7, 2004

(54) COMPOSITIONS AND METHODS FOR IMPROVING KIDNEY FUNCTION

(75) Inventors: Charles E. Hart, Woodinville, WA (US); Stavros Topouzis, Seattle, WA (US)

(73) Assignee: ZymoGenetics, Inc., Seattle, WA (US)

(*) Notice: Subject to any disclaimer, the term of this patent is extended or adjusted under 35 U.S.C. 154(b) by 0 days.

(21) Appl. No.: 10/039,847

(22) Filed: Oct. 26, 2001

(65) Prior Publication Data

US 2002/0183273 A1 Dec. 5, 2002

Related U.S. Application Data

(60) Provisional application No. 60/244,479, filed on Oct. 30, 2000.

(51) Int. Cl.[7] .................. A61K 39/00; A61K 38/00; C07K 14/00
(52) U.S. Cl. .................. 424/198.1; 514/2; 530/350; 530/399
(58) Field of Search .................. 424/198.1; 514/2; 530/350, 399

(56) References Cited

U.S. PATENT DOCUMENTS

| | | | |
|---|---|---|---|
| 6,468,543 B1 | * 10/2002 | Gilbertson et al. | 424/198.1 |
| 6,495,668 B1 | * 12/2002 | Gilbert et al. | 530/399 |

FOREIGN PATENT DOCUMENTS

| | | |
|---|---|---|
| WO | WO 00/27879 | 5/2000 |
| WO | WO 00/59940 | 10/2000 |
| WO | WO 01/25437 | 4/2001 |
| WO | WO 01/89450 | 11/2001 |
| WO | 02/47713 | 6/2002 |

OTHER PUBLICATIONS

Lindberg et al. Seminars in Nephrology vol. 19 (2), 1999, pp. 115–122.*
Johnson, et al., *J. Exp. Med.* 175: 1413–1416, 1992.
Anderson, et al., *Am. J. Physiol.* 274 (Renal Physiol. 43):F463–F472, 1998.
Yagi, et al., *Gen. Pharmac.* 31(5):765–773, 1998.
Deuel, et al., *New Engl J. Med.* 317(4): 236–237, 1987.
Isaka, Y., et al., *J. Clin. Ivest.* 92:2597–2601, 1993.
Floege, J., et al., *J. Clin. Invest.* 9292:2952–2962, 1993.
Nakagawa, T., et al., *Am. J. Pathol.* 155(5): 1689–1699, 1999.
Eddy, A., *Pediatr. Nephrol.* 15:290–301, 2000.
U.S. patent application Ser. No. 09/808,972, Hart et al., filed Mar. 14, 2001.

* cited by examiner

*Primary Examiner*—Janet Andres
(74) *Attorney, Agent, or Firm*—Gary E. Parker

(57) ABSTRACT

Materials and methods for improving kidney function or enhancing proliferation or survival of kidney tubule epithelial cells or epithelial cell precursors in a mammal are disclosed. The methods comprise administering to the mammal a composition comprising a therapeutically effective amount of a zvegf4 protein or a zvegf4 protein-encoding polynucleotide in combination with a pharmaceutically acceptable delivery vehicle. Zvegf4 proteins include, for example, disulfide-bonded dimers of two polypeptide chains, each comprising residues 258–370 of SEQ ID NO:2.

7 Claims, 8 Drawing Sheets

COMPOSITIONS AND METHODS FOR IMPROVING KIDNEY FUNCTION

CROSS-REFERENCE TO RELATED APPLICATION

Figure 1A:
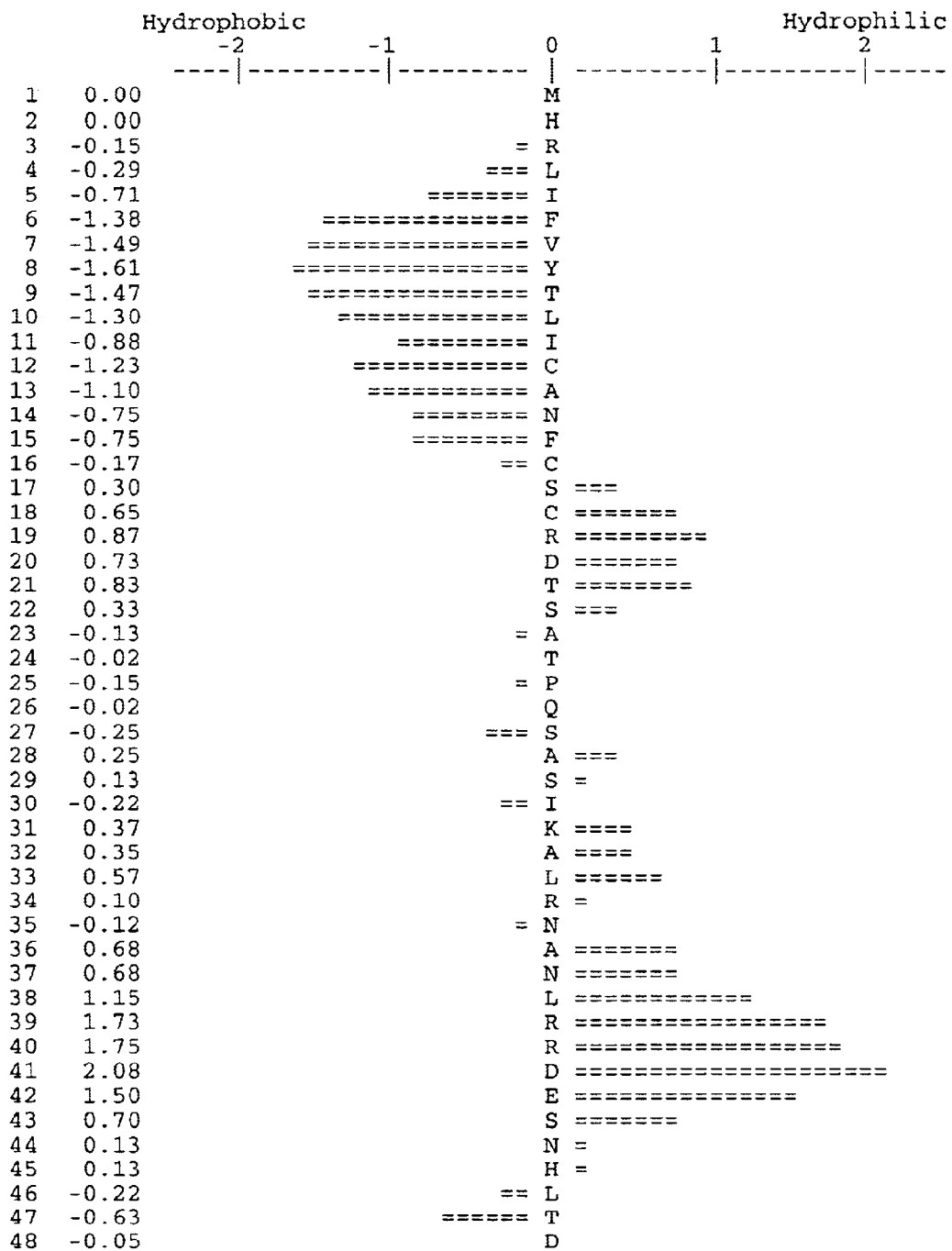
Figure 1H:
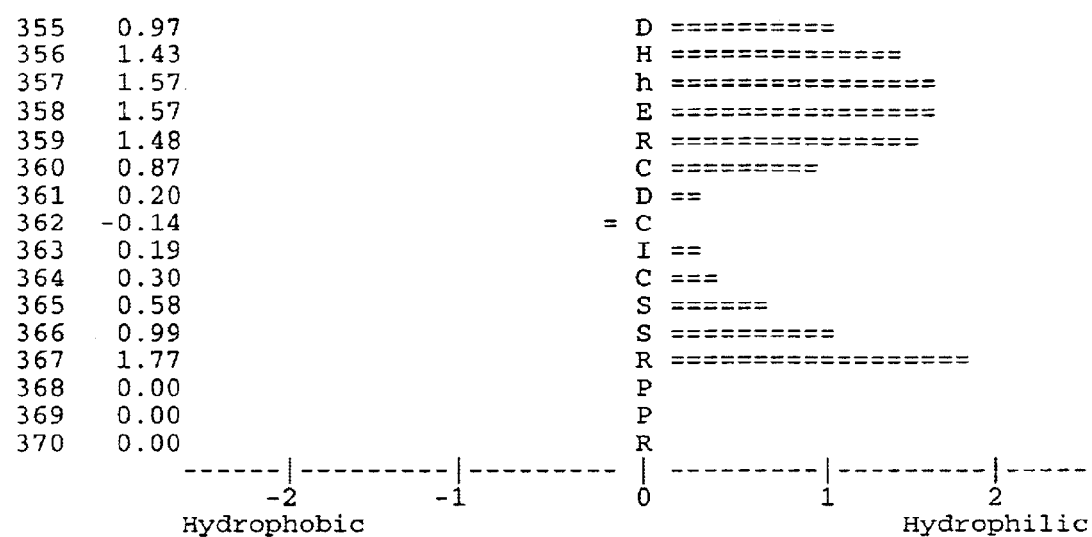

This application claims the benefit under 35 U.S.C. §119 (e) of provisional application No. 60/244,479, filed Oct. 30, 2000.

BACKGROUND OF THE INVENTION

Renal failure can occur as a complication of trauma, shock, poisoning, acute pancreatitis, septicemia, chronic exposure to certain drugs, poisoning, and other causes. Acute tubular necrosis (ATN), the most common cause of acute renal failure, usually occurs after a period of inadequate blood flow to the peripheral organs. Anoxia or poisoning leads to death of tubular epithelial cells and progression to acute renal failure. Chronic analgesic nephritis, which results from prolonged exposure to combinations of phenacetin, aspirin, and acetominophen, may also be due to necrosis of tubular epithelial cells. See, Robbins et al., *Basic Pathology*, Third Edition, W. B. Saunders Co., Philadelphia, 1981, 421–456.

Ischemia- and nephrotoxin-induced renal damages are the main causes of acute renal failure and are characterized by structural and functional damages to renal tubular epithelial cells, predominantly to the proximal tubuli (Oliver et al., *J. Clin. Invest.* 30:1307–1439, 1951). Damage to the proximal tubular epithelium is repaired by a complex regeneration process. After cell desquamation, dedifferentiated proximal tubular cells proliferate and migrate into the denuded area of the basement membrane to establish a new epithelium (Wallin et al., *Lab Invest.* 66:474–484, 1992). In many respects, this nephrogenic repair process resembles the late stage of the development of nephrons, when the embryonic mesenchyme converts to a tubular epithelium (Wallin et al., ibid.; Hammermann et al., *A. J. Physiol.* 262:F523–532, 1992).

While a functional tubular epithelium may be regenerated in as little as 2 weeks, the clinical course of ATN is prolonged in many patients, and treatment consists of supportive care, including dialysis. Without adequate treatment, ATN results in death.

There remains a need in the art for compositions and methods for stimulating the proliferation of kidney tubule epithelial cells in vivo, and thereby improving kidney function.

DESCRIPTION OF THE INVENTION

The present invention provides materials and methods for improving kidney function or enhancing proliferation or survival of kidney tubule epithelial cells or epithelial cell precursors in a mammal.

Within one aspect of the invention there is provided a method of improving kidney function in a mammal in need thereof, comprising administering to the mammal a composition comprising a therapeutically effective amount of a zvegf4 protein or a zvegf4 protein-encoding polynucleotide in combination with a pharmaceutically acceptable delivery vehicle.

Within a second aspect of the invention there is provided a method of enhancing proliferation or survival of kidney tubule epithelial cells or epithelial cell precursors in a mammal, comprising administering to the mammal a composition comprising a therapeutically effective amount of a zvegf4 protein or a zvegf4 protein-encoding polynucleotide in combination with a pharmaceutically acceptable delivery vehicle.

Within certain embodiments of the above-disclosed methods, a zvegf4 protein is administered to the mammal. Within selected embodiments, the zvegf4 protein is a disulfide-bonded dimer of two polypeptide chains, each of the chains comprising residues 258–370 of SEQ ID NO:2, residues 250–370 of SEQ ID NO:2, or residues 246–370 of SEQ ID NO:2. Within other embodiments the zvegf4 protein is a disulfide-bonded dimer of two polypeptide chains, each of the chains consisting of residues X to 370 of SEQ ID NO:2, wherein X is an integer from 246 to 258, inclusive, and wherein the protein is optionally glycosylated.

Within other embodiments of the above-disclosed methods, a zvegf4 protein-encoding polynucleotide is administered to the mammal. Within selected embodiments, the polynucleotide encodes a polypeptide comprising residues 258–370 of SEQ ID NO:2, residues 19–370 of SEQ ID NO:2, or residues 1–370 of SEQ ID NO:2. Within other embodiments, the polynucleotide is a viral vector or plasmid.

Within other embodiments of the invention, the zvegf4 protein is a disulfide-bonded dimer of two polypeptide chains, each of the chains consisting of residues x–y of SEQ ID NO:2, inclusive, wherein the protein is optionally glycosylated, and wherein x is selected from the group consisting of 16, 17, 18, 19, 20, 21, 22, 24, 25, 35, 52, 175, 176, 177, 178, 179, 180, 181, 182, 183, 184, 185, 246, 250, 253, 254, 255, 256, 257, 258, 259, 260, 261, 262, and 263; and y is selected from the group consisting of 365, 366, 367, 368, 369, and 370.

Within other embodiments of the above-disclosed methods, the mammal is suffering from acute tubular necrosis.

These and other aspects of the invention will become evident upon reference to the following detailed description of the invention and the accompanying Figure.

The Figure is a Hopp/Woods hydrophilicity profile of the amino acid sequence shown in SEQ ID NO:2. The profile is based on a sliding six-residue window. Buried G, S, and T residues and exposed H, Y, and W residues were ignored. These residues are indicated in the figure by lower case letters.

"Conservative amino acid substitutions" are defined by the BLOSUM62 scoring matrix of Henikoff and Henikoff, *Proc. Natl. Acad. Sci. USA* 89:10915–10919, 1992, an amino acid substitution matrix derived from about 2,000 local multiple alignments of protein sequence segments, representing highly conserved regions of more than 500 groups of related proteins. As used herein, the term "conservative amino acid substitution" refers to a substitution represented by a BLOSUM62 value of greater than–1. For example, an amino acid substitution is conservative if the substitution is characterized by a BLOSUM62 value of 0, 1, 2, or 3. Preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

A "polypeptide" is a polymer of amino acid residues joined by peptide bonds, whether produced naturally or synthetically. Polypeptides of less than about 10 amino acid residues are commonly referred to as "peptides".

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless. Thus, a protein "consisting of", for example, from 15 to 1500 amino acid residues may further contain one or more carbohydrate chains.

The terms "treat" and "treatment" are used broadly to denote therapeutic and prophylactic interventions that favorably alter a pathological state, including alleviating symptoms thereof. Treatments include procedures that moderate or reverse the progression of, reduce the severity of, prevent, or cure a disease.

The term "zvegf4 protein" is used herein to denote a protein comprising the growth factor domain of a zvegf4 polypeptide (e.g., residues 258–370 of human zvegf4 (SEQ ID NO:2) or mouse zvegf4 (SEQ ID NO:4)), wherein said protein or a proteolytically activated form thereof is mitogenic for cells expressing cell-surface PDGF α- and/or β-receptor subunit. Zvegf4 has been found to activate the αα, αβ, and ββ isoforms of PDGF receptor. Zvegf4 proteins include homodimers and heterodimers as disclosed below. Using methods known in the art, zvegf4 proteins can be prepared in a variety of forms, including glycosylated or non-glycosylated, pegylated or non-pegylated, with or without an initial methionine residue, and as fusion proteins as disclosed in more detail below.

A "zvegf4 protein-encoding polynucleotide" is a polynucleotide that encodes, upon expression by a host cell, a zvegf4 polypeptide that is post-translationally processed to yield a dimeric zvegf4 protein as defined above. Post-translational processing events include, without limitation, disulfide bond formation, proteolysis (including secretory peptide removal), and carbohydrate addition. Those skilled in the art will recognize that the primary translation product of a zvegf4 protein-encoding polynucleotide will ordinarily differ in structure from the final protein. In addition, zvegf4 protein-encoding polynucleotides may include operably linked transcription promoters, terminators, and other genetic elements that provide for expression and/or maintenance of the polynucleotide within the host cell or delivery into the host cell.

All references cited herein are incorporated by reference in their entirety.

The present invention provides methods for improving kidney function in a patient using zvegf4. Zvegf4 is a protein that is structurally related to platelet-derived growth factor (PDGF) and the vascular endothelial growth factors (VEGF). This protein is also referred to as "PDGF-D" (WIPO Publication WO 00/27879). Zvegf4 is a multi-domain protein with significant homology to the PDGF/VEGF family of growth factors.

Structural predictions based on the zvegf4 sequence and its homology to other growth factors suggests that the polypeptide can form homomultimers or heteromultimers that act on tissues by modulating cell proliferation, migration, differentiation, or metabolism. Experimental evidence supports these predictions. Zvegf4 heteromultimers may comprise a polypeptide from another member of the PDGF/VEGF family of proteins, including VEGF, VEGF-B, VEGF-C, VEGF-D, zvegf3/ PDGF-C (WO 00/34474), PlGF (Maglione et al., *Proc. Natl. Acad. Sci. USA* 88:9267–9271, 1991), PDGF-A (Murray et al., U.S. Pat. No. 4,899,919; Heldin et al., U.S. Pat. No. 5,219,759), or PDGF-B (Chiu et al., *Cell* 37:123–129, 1984; Johnsson et al., *EMBO J.* 3:921–928, 1984).

The zvegf4 polypeptide chain comprises a growth factor domain and a CUB domain. The growth factor domain is characterized by an arrangement of cysteine residues and beta strands that is characteristic of the "cystine knot" structure of the PDGF family. The CUB domain shows sequence homology to CUB domains in the neuropilins (Takagi et al., *Neuron* 7:295–307, 1991; Soker et al., *Cell* 92:735–745, 1998), human bone morphogenetic protein-1 (Wozney et al., *Science* 242:1528–1534, 1988), porcine seminal plasma protein and bovine acidic seminal fluid protein (Romero et al., *Nat. Struct. Biol.* 4:783–788, 1997), and *X. laevis* tolloid-like protein (Lin et al., *Dev. Growth Differ.* 39:43–51, 1997).

A representative human zvegf4 polypeptide sequence is shown in SEQ ID NO:2, and a representative mouse zvegf4 polypeptide sequence is shown in SEQ ID NO:4. DNAs encoding these polypeptides are shown in SEQ ID NOS:1 and 3, respectively. Analysis of the amino acid sequence shown in SEQ ID NO:2 indicates that residues 1 to 18 form a secretory peptide. The CUB domain extends from residue 52 to residue 179. A propeptide-like sequence extends from residue 180 to either residue 245, residue 249 or residue 257, and includes four potential cleavage sites at its carboxyl terminus, monobasic sites at residue 245 and residue 249, a dibasic site at residues 254–255, and a target site for furin or a furin-like protease at residues 254–257. Protein produced in a baculovirus expression system showed cleavage between residues 249 and 250, as well as longer species with amino termini at residues 19 and 35. The growth factor domain extends from residue 258 to residue 370, and may include additional residues at the N-terminus (e.g., residues 250 to 257 or residues 246 to 257). Those skilled in the art will recognize that domain boundaries are somewhat imprecise and can be expected to vary by up to ±5 residues from the specified positions. Corresponding domains in mouse and other non-human zvegf4s can be determined by those of ordinary skill in the art from sequence alignments. Cleavage of full-length human zvegf4 with plasmin resulted in activation of the zvegf4 polypeptide. By Western analysis, a band migrating at approximately the same size as the growth factor domain was observed.

Signal peptide cleavage is predicted to occur in human zvegf4 after residue 18 (±3 residues). Upon comparison of human and mouse zvegf4 sequences, alternative signal peptide cleavage sites are predicted after residue 23 and/or residue 24. This analysis suggests that the zvegf4 polypeptide chain may be cleaved to produce a plurality of monomeric species, some of which are shown in Table 1. In certain host cells, cleavage after Lys-255 is expected to result in subsequent removal of residues 254–255, although polypeptides with a carboxyl terminus at residue 255 may also be prepared. Cleavage after Lys-257 is expected to result in subsequent removal of residue 257. Actual cleavage patterns are expected to vary among host cells.

TABLE 1

| Monomer | Residues (SEQ ID NO:2) |
|---|---|
| Cub domain + interdomain region + growth factor domain | 19–370 |
| | 24–370 |
| | 25–370 |
| | 35–370 |
| | 52–370 |

TABLE 1-continued

| Monomer | Residues (SEQ ID NO:2) |
|---|---|
| Growth factor domain | 246–370 |
|  | 250–370 |
|  | 258–370 |
| Growth factor domain + interdomain region | 180–370 |

Zvegf4 can thus be prepared in a variety of multimeric forms comprising a zvegf4 polypeptide as disclosed above. These zvegf4 polypeptides include $zvegf4_{19-370}$, $zvegf4_{52-370}$, $zvegf4_{246-370}$, $zvegf4_{250-370}$, and $zvegf4_{258-370}$. Variants and derivatives of these polypeptides can also be prepared as disclosed herein.

Expression of a zvegf4 polynucleotide in cultured mammalian cells results in the production of a disulfide-bonded, dimeric protein that may be proteolytically processed. The mitogenically active protein is generated upon proteolytic processing to remove the CUB and interdomain regions. An active growth factor domain dimer can be produced directly by expressing a truncated polynucleotide.

Zvegf4 proteins can be prepared as fusion proteins comprising amino- or carboxyl-terminal extensions, such as an amino-terminal methionine residue, an affinity tag, or a targetting polypeptide. For example, a zvegf4 protein can be prepared as a fusion with an affinity tag to facilitate purification. In principal, any peptide or protein for which an antibody or other specific binding agent is available can be used as an affinity tag. Affinity tags include, for example, a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), a Glu-Glu affinity tag (Grussenmeyer et al., *Proc. Natl. Acad. Sci. USA* 82:7952–4, 1985), substance P, FLAG™ peptide (Hopp et al., *Biotechnology* 6:1204–1210, 1988), streptavidin binding peptide, maltose binding protein (Guan et al., *Gene* 67:21–30, 1987), cellulose binding protein, thioredoxin, ubiquitin, T7 polymerase, or other antigenic epitope or binding domain. Fusion of zvegf4 to, for example, maltose binding protein or glutatione S transferase can be used to improve yield in bacterial expression systems. In these instances the non-zvegf4 portion of the fusion protein ordinarily will be removed prior to use. Separation of the zvegf4 and non-zvegf4 portions of the fusion protein is facilitated by providing a specific cleavage site between the two portions. Such methods are well known in the art. Zvegf4 can also be fused to a targetting peptide, such as an antibody (including polyclonal antibodies, monoclonal antibodies, antigen-binding fragments thereof such as $F(ab')_2$ and Fab fragments, single chain antibodies, and the like) or other peptidic moiety that binds to a target tissue.

Variations can be made in the zvegf4 amino acid sequences shown in SEQ ID NO:2 and SEQ ID NO:4 to provide biologically active varaints of zvegf4 proteins. Such variations include amino acid substitutions, deletions, and insertions. In general, conservative amino acid substitutions are preferred. While not wishing to be bound by theory, it is believed that residues within regions 273–295 and 307–317 of human zveg4 (SEQ ID NO:2) may be involved in ligand-receptor interactions. The effects of amino acid sequence changes at specific positions in zvegf4 proteins can be assessed using procedures known in the art, such as site-directed mutagenesis or alanine-scanning mutagenesis (Cunningham and Wells, *Science* 244, 1081–1085, 1989; Bass et al., *Proc. Natl. Acad. Sci. USA* 88:4498–4502, 1991). Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–2156, 1989). Other methods that can be used include phage display (e.g., Lowman et al., *Biochem.* 30:10832–10837, 1991; Ladner et al., U.S. Pat. No. 5,223,409; Huse, WIPO Publication WO 92/06204), region-directed mutagenesis (Derbyshire et al., *Gene* 46:145, 1986; Ner et al., *DNA* 7:127, 1988), and DNA shuffling as disclosed by Stemmer (*Nature* 370:389–391, 1994) and Stemmer (*Proc. Natl. Acad. Sci. USA* 91:10747–10751, 1994). The resultant mutant molecules are tested for receptor binding, mitogenic activity, or other properties (e.g., stimulation of growth factor production) to identify amino acid residues that are critical to these functions. Mutagenesis can be combined with high volume or high-throughput screening methods to detect biological activity of zvegf4 variant polypeptides.

Zvegf4 variants can be analyzed for receptor binding activity by a variety of methods well known in the art, including receptor competition assays (Bowen-Pope and Ross, *Methods Enzymol.* 109:69–100, 1985) and through the use of soluble receptors, including receptors produced as IgG fusion proteins (U.S. Pat. No. 5,750,375). Receptor binding assays can be performed on cell lines that contain known cell-surface receptors for evaluation. The receptors can be naturally present in the cell, or can be recombinant receptors expressed by genetically engineered cells.

Activity of zvegf4 variants can be measured in vitro using cultured cells. For example, mitogenic activity can be measured using known assays, including $^3$H-thymidine incorporation assays (as disclosed by, e.g., Raines and Ross, *Methods Enzymol.* 109:749–773, 1985 and Wahl et al., *Mol. Cell Biol.* 8:5016–5025, 1988), dye incorporation assays (as disclosed by, for example, Mosman, *J. Immunol. Meth.* 65:55–63, 1983 and Raz et al., *Acta Trop.* 68:139–147, 1997) or cell counts. Suitable mitogenesis assays measure incorporation of $^3$H-thymidine into (1) 20% confluent cultures to look for the ability of zvegf4 proteins to further stimulate proliferating cells, and (2) quiescent cells held at confluence for 48 hours to look for the ability of zvegf4 proteins to overcome contact-induced growth inhibition. Suitable dye incorporation assays include measurement of the incorporation of the dye Alamar blue (Raz et al., ibid.) into target cells. See also, Gospodarowicz et al., *J. Cell. Biol.* 70:395–405, 1976; Ewton and Florini, *Endocrinol.* 106:577–583, 1980; and Gospodarowicz et al., *Proc. Natl. Acad. Sci. USA* 86:7311–7315, 1989. Activity can also be assayed by measuring metabolic changes in target cells, such as changes in production of other proteins (including other growth factors) by immunological assays.

The biological activities of zvegf4 variants can be studied in non-human animals by administration of exogenous protein or by expression of zvegf4 variant polynucleotides. Viral delivery systems (disclosed below) can be employed. Zvegf4 variants can be administered or expressed individually, in combination with other zvegf4 proteins, or in combination other compounds, including other growth factors. Test animals are monitored for changes in such parameters as clinical signs, body weight, blood cell counts, clinical chemistry, histopathology, and the like.

Zvegf4 proteins, including full-length polypeptides, variant polypeptides, biologically active fragments, and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms). Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., eds., *Current Protocols in Molecular Biology*, Green and Wiley and Sons, NY, 1993. In general, a DNA sequence encoding a zvegf4 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers. See, for example, WO 00/34474. Exemplary expression systems include yeasts, such as *Saccharomyces cerevisiae* (see, e.g., U.S. Pat. No. 5,527,668) or *Pichia methanolica* (U.S. Pat. Nos. 5,716,808, 5,736,383, 5,854,039, and 5,955,349); mammalian cells, such as baby hamster kidney (BHK) cells (ATCC™ No. CRL 1632 or No. CRL 10314), COS-1 cells (ATCCT™ No. CRL 1650), COS-7 cells (ATCC™ No. CRL 1651), 293 cells (ATCC™ No. CRL 1573; Graham et al., *J. Gen. Virol.* 36:59–72, 1977) or Chinese hamster ovary cells (e.g. CHO-K1, ATCC™ No. CCL 61; or CHO DG44, Chasm et al., *Som. Cell. Molec. Genet.* 12:555, 1986); baculovirus (Luckow et al.,*J. Virol.* 67:4566–4579, 1993; available in kit form BAC-TO-BAC™ kit; LIFE TECHNOLOGIES™, Rockville, Md.)); and bacterial cells (e.g., *E. coli*). Suitable cell lines are known in the art and available from public depositories such as the AMERICAN TYPE CULTURE COLLECT™, Manassas, Va.

Zvegf4 proteins can comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–809, 1993; and Chung et al., *Proc. Natl. Acad. Sci. USA* 90:10145–10149, 1993). In a second method, translation is carried out in Xenopus oocytes by microinjection of mutated mRNA and chemically aminoacylated suppressor tRNAs (Turcatti et al., *J. Biol. Chem.* 271:19991–19998, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–7476, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

Zvegf4 polypeptides or fragments thereof can also be prepared through chemical synthesis according to methods known in the art, including exclusive solid phase synthesis, partial solid phase methods, fragment condensation or classical solution synthesis. See, for example, Merrifield,*J. Am. Chem. Soc.* 85:2149, 1963; Stewart et al., *Solid Phase Peptide Synthesis* (2nd edition), Pierce Chemical Co., Rockford, Ill., 1984; Bayer and Rapp, *Chem. Pept. Prot.* 3:3, 1986; and Atherton et al., *Solid Phase Peptide Synthesis: A Practical Approach*, IRL Press, Oxford, 1989.

Zvegf4 proteins are purified by conventional protein purification methods, typically by a combination of chromatographic techniques. See, in general, *Affinity Chromatography: Principles & Methods*, Pharmacia LKB Biotechnology, Uppsala, Sweden, 1988; and Scopes,*Protein Purification: Principles and Practice*, Springer-Verlag, N.Y., 1994. Proteins comprising a polyhistidine affinity tag (typically about 6 histidine residues) are purified by affinity chromatography on a nickel chelate resin. See, for example, Houchuli et al., *Bio/Technol.* 6: 1321–1325, 1988. Proteins comprising a glu-glu tag can be purified by immunoaffinity chromatography according to conventional procedures. See, for example, Grussenmeyer et al., *Proc. Natl. Acad. Sci. USA* 82:7952–4, 1985. Maltose binding protein fusions are purified on an amylose column according to methods known in the art.

Zvegf4 is highly expressed in the kidney as shown by Northern blotting and PCR analysis. As shown in more detail in the examples that follow, over-expression of zvegf4 in mice by injection of an adenovirus vector encoding zvegf4 elicits tubular epithelial cell proliferation in the kidney. Tubular generation in the treated animals was characterized by the presence of tubular epithelial cells with increased basophilia. These changes were not observed in animals that were exposed to a control adenovirus expressing an unrelated protein. These findings indicate that an increase in zvegf4 protein can modify the function of, and the interactions among, mesangial cells (a type of myofibroblast; see, Powell et al., *Am. J. Physiol.* 277 (*Cell Physiol.* 46):C1–C19, 1999), epithelial cells, endothelial cells, smooth muscle cells, and interstitial cells, which are all key players in glomerular and vascular diseases of the kidney. Furthermore, zvegf4 has been found to affect cell proliferation in at least some of these cells in vitro. Experiments have also shown that the activity of zvegf4 is mediated by two PDGF receptor subunits, alpha and beta (PDGF-αR and PDGF-βR). These receptor subunits are widely expressed in most renal cell types, and their expression is upregulated in a number of kidney pathologies (e.g., Iida et al., *Proc. Natl. Acad. Sci. USA* 88:6560–6564, 1991). The experiments summarized above and disclosed in more detail herein suggest that zvegf4 proteins have a positive effect on renal tubule viability, regeneration, and/or function. These results indicate that zvegf4 may be useful in reversing certain forms of renal failure, such as acute tubular necrosis or chronic analgesic nephritis. In this context, zvegf4 protein may be delivered directly to a mammal or may be produced in situ following delivery to a mammal of a zvegf4 protein-encoding polynucleotide.

While not wishing to be bound by theory, the generative effects of zvegf4 on renal tubules may be due to direct or indirect effects on epithelial cells and/or epithelial cell precursors. "Indirect effects" include the stimulation of production of other factors that act directly on the affected cells. Zvegf4 may stimulate cell proliferation, enhance cell survival, or stimulate the production of other factors that exert these effects on epithelial cells or epithelial cell precursors. Myofibroblasts, for example, are known to secrete cytokines and growth factors that stimulate proliferation, differentiation, and migration of epithelial cells, and to play key roles in organogenesis and wound healing. See, for example, Powell et al., ibid.; Nakagawa et al., *Am. J. Pathol.* 155:1689–1699, 1999; and Matsumoto and Nakamura, *Kidney Int.* 59:2023–2038, 2001.

The growth factor domain of zvegf4 has been found to be the active species of the molecule. Proteolytic processing to remove the N-terminal portion of the molecule is required for activation. Within the present invention zvegf protein may be provided as the active growth factor domain alone or as a precursor requiring activation in vivo. Exemplary precursors include, without limitation, zvegf4$_{19-370}$ and zvegf4$_{52-370}$. Fusion proteins and other biologically active zvegf4 variants can also be employed.

For pharmaceutical use, zvegf4 proteins are formulated according to conventional methods. Conventional routes of delivery for pharmaceutical proteins will be employed. Because patients suffering from acute renal failure will ordinarily be undergoing treatment involving intravenous infusion, catheterization, or dialysis, the protein may be administered through existing intravenous lines, catheters, or shunts. Other routes of administration include intravenous, intramuscular, and subcutaneous injection. In general, pharmaceutical formulations will include a zvegf4 protein in combination with a pharmaceutically acceptable vehicle, such as saline, buffered saline, 5% dextrose in water, or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. A "therapeutically effective amount" of a composition is an amount that produces a statistically significant effect, such as a statistically significant reduction in disease progression or a statistically significant improvement in organ function. Within the context of acute renal failure, improvement in organ function is indicated by one or more of decreased uremia, increased creatinine or inulin clearance, restoration of electrolyte balance, and increased urine production. Zvegf4 will commonly be used in a concentration of about 10 to 100 µg/ml of total volume, although concentrations in the range of 1 ng/ml to 1000 µg/ml may be used. The exact dose will be determined by the clinician according to accepted standards, taking into account the nature and severity of the condition to be treated, patient traits, etc.; determination of dose is within the level of ordinary skill in the art. Because acute renal failure is a life-threatening condition, large doses may be employed. The therapeutic formulations will generally be administered over the period required to achieve a beneficial effect, commonly several hours to several weeks. Dosing is continuous or intermittent over the period of treatment. Intravenous administration will be by bolus injection or infusion over a typical period of one to several hours. Sustained release formulations can also be employed.

Zvegf4 therapy may be combined with other agents or clinical techniques appropriate to the restoration of kidney function. For example, zvegf4 may be administered in combination with a vasodilator or in combination with angioplasty to restore circulation in renal arteries.

Gene therapy may be used to provide zvegf4 to a patient. To facilitate expression of zvegf4 in the kidney, a transcription promoter from a gene that is highly expressed in kidney (e.g., erythropoietin gene) may be employed. Therapeutic polynucleotides can be delivered to patients or test animals by way of viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acids. For review, see Becker et al., *Meth. Cell Biol.* 43:161–89, 1994 and Douglas and Curiel, *Science & Medicine* 4:44–53, 1997. The adenovirus system offers several advantages. Adenovirus can (i) accommodate relatively large DNA inserts; (ii) be grown to high-titer; (iii) infect a broad range of mammalian cell types; and (iv) be used with many different promoters including ubiquitous, tissue specific, and regulatable promoters. Because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. When intravenously administered to intact animals, adenovirus primarily targets the liver. If the adenoviral delivery system has an E1 gene deletion, the virus cannot replicate in the host cells. However, the host's tissue (e.g., liver) will express and process (and, if a signal sequence is present, secrete) the heterologous protein.

An alternative method of gene delivery comprises removing cells from the body and introducing a vector into the cells as a naked DNA plasmid. The transformed cells are then re-implanted in the body. Naked DNA vectors are introduced into host cells by methods known in the art, including transfection, electroporation, microinjection, transduction, cell fusion, DEAE dextran, calcium phosphate precipitation, use of a gene gun, or use of a DNA vector transporter. See, Wu et al., *J. Biol. Chem.* 263:14621–14624, 1988; Wu et al., *J. Biol. Chem.* 267:963–967, 1992; and Johnston and Tang, *Meth. Cell Biol.* 43:353–365, 1994.

The invention is further illustrated by the following non-limiting examples.

EXAMPLES

Example 1

Zvegf4 was identified from the sequence of a clone from a human chronic myelogenous leukemia cell (K562) library by its homology to the VEGF family. Additional sequence was elucidated from a long sequence read of a clone from a pituitary library. An antisense expressed sequence tag (EST) for zvegf4 was found, for which its 5' partner was identified. This 5' EST (EST448186; GenBank) appeared to contain the 5' untranslated sequence for zvegf4. A primer was designed from EST448186 to close the gap in the sequence. 20 pm each of oligonucleotides ZC21,987 (SEQ ID NO:5) and ZC21,120 (SEQ ID NO:6) and 1.93 µg of a thyroid library were used in a PCR reaction with 5% DMSO and 1/10 volume of a commercial reagent (GC-MELT™; CLONTECH™ Laboratories, Inc., Palo Alto, Calif.). The reaction was run for 1 minute at 94° C.; then 30 cycles of 94° C., 20 seconds; 67° C., 1 minute; then a final 5-minute incubation at 72° C. A resulting 833-bp product was sequenced and found to be a zvegf4 fragment containing the remainder of the coding sequence with an intiation MET codon, upstream stop codon, and 5' untranslated sequence. The composite sequence included an open reading frame of 1,110 bp (SEQ ID NO:1).

Example 2

A partial mouse zvegf4 sequence was obtained by probing a mouse genomic library (obtained from CLONTECH™ Laboratories, Inc.) with a 1,289 bp EcoRI human zvegf4 restriction digest fragment containing the entire coding sequence. The probe was labeled with $^{32}$P using a commercially available kit (REDIPRIME™ II random-prime labeling system; AMERSHAM PHARMACIA™, Buckinghamshire, England). Unincorporated radioactivity was removed using a commercially available push column (NUCTRAP® column; STRATAGENE™, La Jolla, Calif.; see U.S. Pat. No. 5,336,412). Twenty-four filter lifts were prehybridized overnight at 50° C. in a hybridization solution (EXPRESSHYB™ Hybridization Solution; CLONTECH™ Laboratories, Inc.) containing 0.1 mg/ml salmon sperm DNA that had been boiled 5 minutes, then iced. Filters were hybridized overnight at 50° C. in hybridization solution (EXPRESSHYB™) containing $1.0 \times 10^6$ cpm/ml zvegf4 probe, 0.1 mg/ml salmon sperm DNA, and 0.5 µg/ml mouse cot-1 DNA that had been boiled 5 minutes, then iced. Filter lifts were washed in 2×SSC, 0.1% SDS at room temperature for 2 hours, then the temperature was raised to 60° C. for one hour. Overnight exposure at −80° C. showed 7 putative primary hits.

Four of the primary hits were plated on a lawn of E. coli K802 cells (obtained from CLONTECH™Laboratories, Inc.). Filter lifts were prepared and hybridized overnight with the human zvegf4 probe. Two of the 4 primary putative hits that were tested came up positive.

DNA was prepared from one positive plaque and digested with BamHI and PstI. The digest was run on a 1% Tris-Borate-EDTA gel, and a 2.0 kb doublet and 2.7 kb/2.9 kb bands were excised from the gel and extracted from the agarose by conventional methods. Both 2.0 kb fragments were found to strongly hybridize to the human zvegf4 probe. These fragments were sequenced and found to contain part of the mouse zvegf4 CUB domain. Primers were designed from the sequence for use in a PCR cDNA screen.

A panel of mouse cDNAs was screened by PCR with primers ZC26,317 (SEQ ID NO:7) and ZC26,318 (SEQ ID NO:8). Embryo, salivary gland, neonatal skin, and testis showed strong products of the predicted 200 bp size.

Mouse testis and salivary gland libraries were screened by PCR using primers ZC26,317 (SEQ ID NO:7) and ZC26,318 (SEQ ID NO:8). The testis library yielded one clone, named "zvegf4mpzp7x-6", that was incomplete at the 5' end and appeared to contain an intron at the 5' end. The salivary gland library yielded one clone, named "zvegf4mpzp7x-7", that had a 225-bp deletion in coding compared to clone zvegf4mpzp7x-6. The sequences derived from zvegf4mpzp7x-6 and zvegf4mpzp7x-7 were combined to produce a full-length mouse zvegf4 polynucleotide sequence (SEQ ID NO:3) and mouse zvegf4 polypeptide sequence (SEQ ID NO:4).

A full-length cDNA clone was generated by a two-step ligation of fragments from the two clones. An EcoRI/HindIII 3' fragment was prepared from clone zvegf4mpzp7x-6. The 528-bp fragment was gel-purified and ligated into a phagemid vector (PBLUESCRIPT® II KS(+); STRATAGENE™) that had been digested with EcoRI and HindIII. Three µg of the resulting construct was digested with 15 units of EcoRI. The linearized plasmid was purified and ligated with a 754-bp 5' EcoRI fragment from clone zvegf4mpzp7x-7.

Example 3

Recombinant human zvegf4 having a carboxyl-terminal Glu-Glu affinity tag was produced in a baculovirus expression system according to conventional methods. The culture was harvested, and the cells were lysed with a solution of 0.02 M Tris-HCl, pH 8.3, 1 mM EDTA, 1 mM DTT, 1 mM 4-(2-Aminoethyl)-benzenesulfonyl fluoride hydrochloride (PEFABLOC® SC; Boehringer-Mannheim), 0.5 µM aprotinin, 4 mM leupeptin, 4 mM E-64, 1% NP-40 at 4° C. for 15 minutes on a rotator. The solution was centrifuged, and the supernatant was recovered. Twenty ml of extract was combined with 50 µl of anti-Glu-Glu antibody conjugated to derivatized agarose beads (SEPHAROSE®; AMERSHAM PHARMACIA™ Biotech Inc., Piscataway, N.J.) in 50 µl buffer. The mixture was incubated on a rotator at 4° C. overnight. The beads were recovered by centrifugation and washed 3×15 minutes at 4° C. Pellets were combined with sample buffer containing reducing agent and heated at 98° C. for five minutes. The protein was analyzed by polyacrylanude gel electrophoresis under reducing conditions followed by western blotting on a PVDF membrane using an antibody to the affinity tag. Two bands were detected, one at $M_r \approx 49$ kD and the other at $M_r \approx 21$ kD. Sequence analysis showed the larger band to comprise two sequences, one beginning at Arg-19 of SEQ ID NO:2 and the other beginning at Asn-35 of SEQ ID NO:2. The asparagine residue appeared to have been deamidated to an aspartic acid. The smaller band began at Ser-250 of SEQ ID NO:2.

Example 4

Recombinant amino-terminally Glu-Glu-tagged zvegf4 growth factor domain with an amino-terminal Glu-Glu (EYMPME; SEQ ID NQ:9) tag (zvegf4-nee-GFD) produced from recombinant baculovirus-infected insect cells was purified from the conditioned media by a combination of cation-exchange chromatography, antibody affinity chromatography, and size-exclusion chromatography. 28-liter cultures were harvested, and the media were filtered using a 0.45 µm filter. Filtered medium (pH 7.0, conductivity 9 mS) was directly loaded onto a 25-ml cation exchange column (POROS® 50 HS; PerSeptive Biosystems, Framiugham, Mass.). The column was washed with ten column volumes (cv) of PBS, and the bound protein was eluted with a gradient of 20–100% of 750 mM NaCl in PBS (Buffer B) for 15 cv followed by 5 cv of 100% Buffer B at 5 ml/mm. Five-ml fractions were collected. Samples from the column were analyzed by SDS-PAGE with silver staining and western blotting for the presence of zvegf4-nee-GFD. Zvefg4-nee-GFD-containing fractions were pooled and loaded onto an 8-ml anti-GIu-Glu antibody column and eluted with 50 ml of 0.5 mg/ml EYMPTD (SEQ ID NO:10)

peptide (obtained from Princeton Biomolecules Corporation, Langhorne, Pa.) in PBS. One-ml fractions were pooled and concentrated to 4 ml using using a BIOMAX™-5 concentrator (MILLIPORE™ Corp., Bedford, Mass.) and loaded onto a 16×1000 mm gel filtration column (SEPHACRYL™ S-100 HR; AMERSHAM PHARMACIA™ Biotech, Piscataway, N.J.) at 1.5 ml/minute. Five-ml fractions containing purified zvegf4-nee-GFD were pooled, filtered through a 0.2 $\mu$m filter, aliquoted into 100 $\mu$l aliquots, and frozen at −80° C. The concentration of the final purified protein was determined by BCA assay (Pierce Chemical Co., Rockford, Ill.) to be 0.4 mg/ml, and the yield was calculated to be 8.4 mg.

Recombinant zvegf4-nee-GFD was analyzed by SDS-PAGE (NUPAGE™ 4–12% gel; NOVEX™, San Diego, Calif.) with silver staining (FASTSILVER™, Geno Technology, Inc., Maplewood, Mo.) and Western blotting using antibodies to the peptide tag. Conditioned media or purified protein was electrophoresed using an electrophoresis mini-cell (XCell II™ mini-cell; NOVEX™) and transferred to nitrocellulose (0.2 $\mu$m; NOVEX) at room temperature using a blot module (XCell II™; NOVEX™) with stirring according to directions provided in the instrument manual. The transfer was run at 500 mA for one hour in a buffer containing 25 mM Tris base, 200 mM glycine, and 20% methanol. The filters were then blocked with 10% non-fat dry milk in PBS for 10 minutes at room temperature. The nitrocellulose was quickly rinsed, then the mouse anti-peptide primary antibody (diluted 1:1000 in PBS containing 2.5% non-fat dry milk) was added. The blots were incubated for two hours at room temperature or overnight at 4° C. with gentle shaking. Following the incubation, blots were washed three times for 10 minutes each in PBS, then labeled with a secondary antibody (goat anti-mouse IgG conjugated to horseradish peroxidase) diluted 1:1000 in PBS containing 2.5% non-fat dry milk, and the blots were incubated for two hours at room temperature with gentle shaking. The blots were then washed three times, 10 minutes each, in PBS, then quickly rinsed with $H_2O$. The blots were developed using commercially available chemiluminescent substrate reagents (SUPERSIGNAL® ULTRA reagents 1 and 2 mixed 1:1; reagents obtained from Pierce Chemical Co.), and the signal was captured using image analysis software (Lumi-Imager™ Lumi Analyst 3.0; Boehringer Mannheim GmbH, Germany) for times ranging from 10 seconds to 5 minutes or as necessary.

The purified zvefg4-nee-GFD appeared as two bands on the silver-stained gel at about 31 and 17 kDa under non-reducing conditions and as a single band of 17 kDa under reducing conditions. This suggested existence of a dimeric form of zvegf4-nee-GFD under non-reducing conditions. The purified protein consisted of approximately 90% dimer and 10% monomer.

Example 5

Full-length carboxyl-terminal Glu-Glu tagged zvegf4 (zvegf4-cee) was produced from recombinant baculovirus-infected insect cells. Two-liter cultures were harvested, and the media were sterile-filtered using a 0.2 $\mu$m filter.

Protein was purified from the conditioned media by a combination of anti-Glu-Glu (anti-EE) peptide antibody affinity chromatography and S-200 gel exclusion chromatography. Culture media (pH 6.0, conductivity 7 mS) was directly loaded onto a 20×80 mm (25-ml bed volume) anti-EE antibody affinity column at a flow of 6 ml/minute. The column was washed with ten column volumes of PBS, then bound protein was eluted with two column volumes of 0.4 mg/ml EYMPTD peptide (SEQ ID NO:10) (Princeton BioMolecules Corp., Langhorne, Pa.). Five-ml fractions were collected. Samples from the anti-EE antibody affinity column were analyzed by SDS-PAGE with silver staining and western blotting (essentially as disclosed above using anti-zvegf4 peptide antibodies and anti-EE antibody and HRP-conjugated goat anti-rabbit secondary antibody) for the presence of zvegf4-cee.

Zvefg4-cee-containing fractions were pooled and concentrated to 3.8 ml by filtration using a BIOMAX™ -5 concentrator (MILLIPORE™Corp.), and loaded onto a 16×1000 mm gel filtration column (SEPHACRYL™ S-200 HR; AMERSHAM PHARMACIA™ Biotech). The fractions containing purified zvegf4-cee were pooled, filtered through a 0.2 $\mu$m filter, aliquoted into 100 $\mu$l each, and frozen at −80° C. The concentration of the final purified protein was determined by colorimetric assay (BCA assay reagents; Pierce Chemical Co.) and HPLC-amino acid analysis.

The purified zvefg4-cee appeared as a single band at about 85 kDa under non-reducing conditions with silver staining, but at about 50 kDa under reducing conditions, suggesting a dimeric form of zvefg4-cee under non-reducing conditions.

Example 6

To prepare adenovirus vectors, the protein coding region of zvegf4 is amplified by PCR using primers that add FseI and AscI restriction sites at the 5' and 3' termini, respectively. PCR primers are used with a template containing the full-length zvegf4 cDNA in a PCR reaction as follows: incubation at 95° C. for 5 minutes; followed by 15 cycles at 95° C. for 1 min., 58° C. for 1 min., and 72° C. for 1.5 min.; followed by 72° C. for 7 min.; followed by a 4° C. soak. The reaction products are loaded onto a 1.2% (low melt) (SEAPLAQUE GTG™; FMC, Rockland, Me.) gel in TAE buffer. The zvegf4 PCR product is excised from the gel and purified using a spin column containing a silica gel membrane (QIAQUICK™ Gel Extraction Kit; QIAGEN™, Inc., Valencia, Calif.) as per kit instructions. The zvegf4 product is then digested, phenol/chloroform extracted, EtOH precipitated, and rehydrated in 20ml TE (Tris/EDTA pH 8). The zvegf4 fragment is then ligated into the cloning sites of the transgenic vector pTG12–8. Vector pTG12–8 was derived from p2999B4 (Palmiter et al., *Mol. Cell Biol.* 13:5266–5275, 1993) by insertion of a rat insulin II intron (ca. 200 bp) and polylinker (Fse I/Pme I/Asc I) into the Nru I site. The vector comprises a mouse metallothionein (MT-1) promoter (ca. 750 bp) and human growth hormone (hGH) untranslated region and polyadenylation signal (ca. 650 bp) flanked by 10 kb of MT-15'flanking sequence and 7 kb of MT-1 3' flanking sequence. The construct is transformed into *E. coli* host cells (ELECTROMAX DH10B™ cells; obtained from LIFE TECHNOLOGIES™, Inc., Gaithersburg, Md.) by electroporation. Clones containing zvegf4 DNA are identified by restriction analysis. A positive clone is confirmed by direct sequencing.

The zvegf4 cDNA is released from the pTG12-8 vector using FseI and AscI enzymes. The cDNA is isolated on a 1% low melt agarose gel, and is then excised from the gel. The gel slice is melted at 70° C., extracted twice with an equal volume of Tris-buffered phenol, and EtOH precipitated. The DNA is resuspended in 1 $\mu$H$_2$O.

The zvegf4 cDNA is cloned into the FseI-AscI sites of a modified pAdTrack CMV (He et al., *Proc. Nat). Acad. Sci.*

USA 95:2509–2514, 1998). This construct contains a green fluorescent protein (GFP) marker gene. The CMV promoter driving GFP expression has been replaced with the SV40 promoter, and the SV40 polyadenylation signal has been replaced with the human growth hormone polyadenylation signal. In addition, the native polylinker has been replaced with FseI, EcoRV, and AscI sites. This modified form of pAdTrack CMV is named pZyTrack. Ligation is performed using a DNA ligation and screening kit (FAST-LINK™; Epicentre Technologies, Madison, Wis.). In order to linearize the plasmid, approximately 5 µg of the pZyTrack zvegf4 plasmid is digested with PmeI. Approximately 1 µg of the linearized plasmid is cotransformed with 200 ng of supercoiled pAdEasy (He et al., ibid.) into BJ5183 cells. The co-transformation is done using a Bio-Rad Gene Pulser at 2.5kV, 200 ohms and 25 µF. The entire co-transformation is plated on 4 LB plates containing 25 µg/ml kanamycin. The smallest colonies are picked and expanded in LB/kanamycin, and recombinant adenovirus DNA is identified by standard DNA miniprep procedures. Digestion of the recombinant adenovirus DNA with FseI and AscI confirms the presence of zvegf4 DNA. The recombinant adenovirus miniprep DNA is transformed into E. coli DH10B competent cells, and DNA is prepared therefrom.

Approximately 5 µg of recombinant adenoviral DNA is digested with PacI enzyme (New England Biolabs) for 3 hours at 37° C. in a reaction volume of 100 µl containing 20–30U of PacI. The digested DNA is extracted twice with an equal volume of phenol/chloroform and precipitated with ethanol. The DNA pellet is resuspended in 10 µl distilled water. A T25 flask of QBI-293A cells (Quantum Biotechnologies, Inc., Montreal, Canada), inoculated the day before and grown to 60–70% confluence, are transfected with the PacI digested DNA. The PacI-digested DNA is diluted up to a total volume of 50 µl with sterile HBS (150 mM NaCl, 20 mM HEPES). In a separate tube, 20 µl of 1 mg/ml N-[1-(2,3-Dioleoyloxy)propyl]-N,N,N-trimethylammonium methylsulfate (DOTAP; Boehringer Mannheim) is diluted to a total volume of 100 µl with HBS. The DNA is added to the DOTAP, mixed gently by pipeting up and down, and left at room temperature for 15 minutes. The media is removed from the 293A cells and washed with 5 ml serum-free MEM-alpha (LIFE TECHNOLOGIES™, Gaithersburg, Md.) containing 1 mM sodium pyruvate (LIFE TECHNOLOGIES™), 0.1 mM MEM non-essential amino acids (Life Technologies) and 25 mM HEPES buffer (LIFE TECHNOLOGIES™). 5 ml of serum-free MEM is added, and the cells are held at 37° C. The DNA/lipid mixture is added drop-wise to the flask, mixed gently, and incubated at 37° C. for 4 hours. After 4 hours the media containing the DNA/lipid mixture is aspirated off and replaced with 5 ml complete MEM containing 5% fetal bovine serum. The transfected cells are monitored for GFP expression and formation of foci (viral plaques).

Seven days after transfection of 293A cells with the recombinant adenoviral DNA, cells expressing GFP start to form foci. The crude viral lysate is collected with a cell scraper to collect the cells. The lysate is transferred to a 50 ml conical tube. To release most of the virus particles from the cells, three freeze/thaw cycles are done in a dry ice/ ethanol bath and a 37° C. waterbath.

Ten 10-cm plates of nearly confluent (80–90%) 293A cells are set up 20 hours prior to infection. The crude lysate is amplified (primary amplification) to obtain a working stock of zvegf4 rAdV lysate. 200 ml of crude rAdV lysate is added to each 10-cm plate, and the plates are monitored for 48 to 72 hours looking for cytopathic effect (CPE) under the white light microscope and expression of GFP under the fluorescent microscope. When all of the cells show CPE, this 1° stock lysate is collected, and freeze/thaw cycles are performed as described above.

Secondary (2°) amplification of zvegf4 rAdV is obtained from twenty 15-cm tissue culture dishes of 80–90% confluent 293A cells. All but 20 ml of 5% MEM media is removed, and each dish is inoculated with 300–500 ml of 10 amplified rAdv lysate. After 48 hours the cells are lysed from virus production, the lysate is collected into 250 ml polypropylene centrifuge bottles, and the rAdV is purified.

NP-40 detergent is added to a final concentration of 0.5% to the bottles of crude lysate to lyse all cells. Bottles are placed on a rotating platform for 10 minutes and agitated as fast as possible. The debris is pelleted by centrifugation at 20,000×G for 15 minutes. The supernatant is transferred to 250-ml polycarbonate centrifuge bottles, and 0.5 volume of 20% PEG8000/2.5M NaCl solution is added. The bottles are shaken overnight on ice. The bottles are centrifuged at 20,000×G for 15 minutes, and the supernatants are discarded into a bleach solution. A white precipitate (precipitated virus/PEG) forms in two vertical lines along the walls of the bottles on either side of the spin mark. Using a sterile cell scraper, the precipitate from 2 bottles is resuspended in 2.5 ml PBS. The virus solution is placed in 2-ml microcentrifuge tubes and centrifuged at 14,000×G in a microcentrifuge for 10 minutes to remove any additional cell debris. The supernatants from the 2-ml microcentrifuge tubes are transferred into a 15-ml polypropylene snapcap tube and adjusted to a density of 1.34 g/ml with CsCl. The volume of the virus solution is estimated, and 0.55 g/ml of CsCl added. The CsCl is dissolved, and 1 ml of this solution weighed. The solution is transferred to polycarbonate, thick-walled, 3.2 ml centrifuge tubes (Beckman) and spun at 348,000×G for 3–4 hours at 25° C. The virus forms a white band. Using wide-bore pipette tips, the virus band is collected.

The virus recovered from the gradient includes a large amount of CsCl, which must be removed before it can be used on cells. PHARMACIA™ PD)-10 columns prepacked with SEPHADEX® G-25M (PHARMACIA™) are used to desalt the virus preparation. The column is equilibrated with 20 ml of PBS. The virus is loaded and allowed to run into the column. 5 ml of PBS is added to the column, and fractions of 8–10 drops collected. The optical density of a 1:50 dilution of each fraction is determined at 260 nm on a spectrophotometer, and a clear absorbance peak is identified. Peak fractions are pooled, and the optical density (OD) of a 1:25 dilution is determined. OD is converted into virus concentration using the formula (OD at 260 nm)(25)(1.1× $10^{12}$)=virions/ml.

To store the virus, glycerol is added to the purified virus to a final concentration of 15%, mixed gently and stored in aliquots at −80° C.

A protocol developed by Quantum Biotechnologies, Inc. (Montreal, Canada) is followed to measure recombinant virus infectivity. Briefly, two 96-well tissue culture plates are seeded with 1×$10^4$ 293A cells per well in MEM containing 2% fetal bovine serum for each recombinant virus to be assayed. After 24 hours, 10-fold dilutions of each virus from 1×$10^2$ to 1×$10^{14}$ are made in MEM containing 2% fetal bovine serum. 100 µl of each dilution is placed in each of 20 wells. After 5 days at 37° C., wells are read either positive or negative for CPE, and PFU/ml is calculated.

$TCID_{50}$ formulation used is as per Quantum Biotechnologies, Inc., above. The titer (T) is determined from a plate where virus used is diluted from $10^{-2}$ to $10^{-14}$, and read 5 days after the infection. At each dilution a ratio (R) of positive wells for CPE per the total number of wells is determined. The titer of the undiluted sample is $T=10^{(I+F)}=TCID_{50}/ml$, where $F=1+a(S-0.5)$, S is the sum of the ratios (R), and d is $Log_{10}$ of the dilution series (e.g., d=1 for a ten-fold dilution series). To convert $TCID_{50}$ ml to pfu/ml, 0.7 is subtracted from the exponent in the calculation for titer (T).

Example 7

The protein-coding region of human zvegf4 DNA was amplified by PCR using primers that added PmeI and AscI restriction sites at the 5' and 3' termini, respectively. The resulting zvegf4 cDNA was cloned into the EcoRV-AscI sites of pZyTrack (Example 6). Recombinant adenovirus was generated in 293A cells and purified on CsCl gradients. Viral particle numbers were determined by spectrophotometry, and infectious particle numbers were determined by $TCID_{50}$ assay. The virus was designated AdZyvegf4.

Eight-week-old C57BL/6 mice were infected with AdZyvegf4 to determine the effects on serum chemistry, complete blood counts (CBC), body and organ weight changes, and histology. On day-1, the mice were tagged, individually weighed, and group normalized for separation into treatment groups (4 mice per cage). Group 1 mice (n=8 females, 7 males) received GFP (control) adenovirus, $1 \times 10^{11}$ particles. Group 2 mice (n=8 females, 6 males) received zvegf4 adenovirus, $1 \times 10^{11}$ particles. Group 3 mice (n=8 females, 8 males) were untreated controls. On day 0, the mice received injections of the appropriate adenovirus solution. On day 10, blood was collected (under ether anesthesia) for CBCs and clinical chemistry measurements. On day 20, mice were weighed and sacrificed by cervical dislocation after collecting blood (under ether anesthesia) for CBCs and clinical chemistry measurements. Selected tissues were fixed and evaluated for morphological changes. The following pathological findings were noted in the majority (80–100%) of the animals treated with the AdZyvegf4 adenovirus, and were not observed in either of the other two groups.

In the liver, there was moderate proliferation of sinusoidal cells, especially cells with small ovoid nuclei and no observable cytoplasm lining the sinusoids that were more clustered in the venous regions of the hepatic lobule. The cells appeared to be spindle Ito (or stellate) cells, which are a major cell type incriminated in the onset and progression of hepatic fibrosis.

In all AdZyvegf4-treated animals, the glomeruli of the kidneys were enlarged and were characterized by hypercellularity of mesangial cells. In addition, all six male mice and four out of seven female mice showed signs of tubular regeneration. These changes were not observed in animals that were exposed to a control adenovirus expressing an unrelated protein. Tubular regeneration was characterized by the presence of tubular epithelial cells with increased basophilia. More detailed histological examination revealed little evidence of tubulointerstitial proliferation or inflammatory cell infiltration.

An increased amount of bronchoalveolar lymphoid tissue was noted in the lungs of the AdZyvegf4-treated animals. Bronchoalveolar lymphoid tissue consisted predominantly of clusters of lymphocytes admixed with fewer numbers of plasma cells around vessels within the lung parenchyma, a sign of lung inflammatory response, which is an important initiator and participant in several forms of lung fibrosis.

In the femur, the majority of animals displayed minimal to severe endosteal bone filling the marrow space, with decreased amounts of hematopoietic elements resulting from loss of marrow space due to the proliferating endosteal bone. In addition, four of six male and two of eight female animals had proliferation of stromal cells, which was characterized by an increased number of spindle-shaped cells.

Example 8

Restoration of kidney function is assessed using the model of Nakagawa et al. (*Am. J. Pathology* 155:1689–1699, 1999). Ischemic tubular injury is induced in male Sprague-Dawley rats weighing 250 to 300 g by clamping bilateral renal arteries for exactly 50 minutes. Core body temperature is maintained at 37±1° C. by placing the animals on a homeothermic table and monitoring with a temperature-sensing rectal probe. After the clamp is released, the kidneys are reperfused for various time intervals. Zvegf4 is administered at various time points after injury. Animal mortality at 1–10 days after surgery is an indication of persistent renal dysfunction. Kidney function can also be assessed by proteinuria, by creatinine levels in serum, and other methods known to those skilled in the art.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of enhancing proliferation or survival of kidney tubule epithelial cells or epithelial cell precursors in a mammal in need thereof, comprising administering to the mammal a composition comprising a therapeutically effective amount of a zvegf4 protein, in combination with a pharmaceutically acceptable delivery vehicle, wherein the zvegf4 protein is a disulfide-bonded dimer of two polypeptide chains, each of said chains consisting of residues x–y of SEQ ID NO:2, inclusive, wherein the protein is optionally glycosylated, and wherein:

x is selected from the group consisting of 16, 17, 18, 19, 20, 21, 22, 24, 25, 35, 52, 175, 176, 177, 178, 179, 180, 181, 182, 183, 184, 185, 246, 250, 253, 254, 255, 256, 257, 258, 259, 260, 261, 262, and 263; and y is selected from the group consisting of 365, 366, 367, 368, 369, and 370.

2. The method of claim 1 wherein x is selected from the group consisting of 19, 24, 25, 35, 52, 180, 246, 250, and 258.

3. The method of claim 1 wherein x is 258±5.

4. The method of claim 1 wherein y is 370.

5. The method of claim 1 wherein x is 258 and y is 370.

6. The method of claim 1 wherein x is 250 and y is 370.

7. The method of claim 1 wherein x is 246 and y is 370.

* * * * *

SEQUENCE LISTING

<160> NUMBER OF SEQ ID NOS: 10

<210> SEQ ID NO 1
<211> LENGTH: 1882
<212> TYPE: DNA
<213> ORGANISM: Homo sapiens
<220> FEATURE:
<221> NAME/KEY: CDS
<222> LOCATION: (226)...(1338)

<400> SEQUENCE: 1
ccgtcaccat ttatcagctc agcaccacaa ggaagtgcgg cacccacacg cgctcggaaa      60

-continued

```
gttcagcatg caggaagttt ggggagagct cggcgattag cacagcgacc cgggccagcg      120
cagggcgagc gcaggcggcg agagcgcagg gcggcgcggc gtcggtcccg ggagcagaac      180
ccggcttttt cttggagcga cgctgtctct agtcgctgat cccaa atg cac cgg ctc      237
                                                Met His Arg Leu
                                                  1
```

```
atc ttt gtc tac act cta atc tgc gca aac ttt tgc agc tgt cgg gac        285
Ile Phe Val Tyr Thr Leu Ile Cys Ala Asn Phe Cys Ser Cys Arg Asp
  5              10                 15                  20 act tct gca acc ccg cag agc gca tcc atc aaa gct ttg cgc aac gcc        333
Thr Ser Ala Thr Pro Gln Ser Ala Ser Ile Lys Ala Leu Arg Asn Ala
                     25                 30                  35 aac ctc agg cga gat gag agc aat cac ctc aca gac ttg tac cga aga        381
Asn Leu Arg Arg Asp Glu Ser Asn His Leu Thr Asp Leu Tyr Arg Arg
             40                 45                 50 gat gag acc atc cag gtg aaa gga aac ggc tac gtg cag agt cct aga        429
Asp Glu Thr Ile Gln Val Lys Gly Asn Gly Tyr Val Gln Ser Pro Arg
         55                 60                 65 ttc ccg aac agc tac ccc agg aac ctg ctc ctg aca tgg cgg ctt cac        477
Phe Pro Asn Ser Tyr Pro Arg Asn Leu Leu Leu Thr Trp Arg Leu His
     70                 75                 80 tct cag gag aat aca cgg ata cag cta gtg ttt gac aat cag ttt gga        525
Ser Gln Glu Asn Thr Arg Ile Gln Leu Val Phe Asp Asn Gln Phe Gly
 85                 90                 95                 100 tta gag gaa gca gaa aat gat atc tgt agg tat gat ttt gtg gaa gtt        573
Leu Glu Glu Ala Glu Asn Asp Ile Cys Arg Tyr Asp Phe Val Glu Val
                    105                 110                 115 gaa gat ata tcc gaa acc agt acc att att aga gga cga tgg tgt gga        621
Glu Asp Ile Ser Glu Thr Ser Thr Ile Ile Arg Gly Arg Trp Cys Gly
                120                 125                 130 cac aag gaa gtt cct cca agg ata aaa tca aga acg aac caa att aaa        669
His Lys Glu Val Pro Pro Arg Ile Lys Ser Arg Thr Asn Gln Ile Lys
            135                 140                 145 atc aca ttc aag tcc gat gac tac ttt gtg gct aaa cct gga ttc aag        717
Ile Thr Phe Lys Ser Asp Asp Tyr Phe Val Ala Lys Pro Gly Phe Lys
        150                 155                 160 att tat tat tct ttg ctg gaa gat ttc caa ccc gca gca gct tca gag        765
Ile Tyr Tyr Ser Leu Leu Glu Asp Phe Gln Pro Ala Ala Ala Ser Glu
165                 170                 175                 180 acc aac tgg gaa tct gtc aca agc tct att tca ggg gta tcc tat aac        813
Thr Asn Trp Glu Ser Val Thr Ser Ser Ile Ser Gly Val Ser Tyr Asn
                    185                 190                 195 tct cca tca gta acg gat ccc act ctg att gcg gat gct ctg gac aaa        861
Ser Pro Ser Val Thr Asp Pro Thr Leu Ile Ala Asp Ala Leu Asp Lys
                200                 205                 210 aaa att gca gaa ttt gat aca gtg gaa gat ctg ctc aag tac ttc aat        909
Lys Ile Ala Glu Phe Asp Thr Val Glu Asp Leu Leu Lys Tyr Phe Asn
            215                 220                 225 cca gag tca tgg caa gaa gat ctt gag aat atg tat ctg gac acc cct        957
Pro Glu Ser Trp Gln Glu Asp Leu Glu Asn Met Tyr Leu Asp Thr Pro
        230                 235                 240 cgg tat cga ggc agg tca tac cat gac cgg aag tca aaa gtt gac ctg       1005
Arg Tyr Arg Gly Arg Ser Tyr His Asp Arg Lys Ser Lys Val Asp Leu
245                 250                 255                 260 gat agg ctc aat gat gat gcc aag cgt tac agt tgc act ccc agg aat       1053
Asp Arg Leu Asn Asp Asp Ala Lys Arg Tyr Ser Cys Thr Pro Arg Asn
                    265                 270                 275 tac tcg gtc aat ata aga gaa gag ctg aag ttg gcc aat gtg gtc ttc       1101
Tyr Ser Val Asn Ile Arg Glu Glu Leu Lys Leu Ala Asn Val Val Phe
                280                 285                 290
```

-continued

```
ttt cca cgt tgc ctc ctc gtg cag cgc tgt gga gga aat tgt ggc tgt      1149
Phe Pro Arg Cys Leu Leu Val Gln Arg Cys Gly Gly Asn Cys Gly Cys
        295                 300                 305 gga act gtc aac tgg agg tcc tgc aca tgc aat tca ggg aaa acc gtg      1197
Gly Thr Val Asn Trp Arg Ser Cys Thr Cys Asn Ser Gly Lys Thr Val
310                 315                 320 aaa aag tat cat gag gta tta cag ttt gag cct ggc cac atc aag agg      1245
Lys Lys Tyr His Glu Val Leu Gln Phe Glu Pro Gly His Ile Lys Arg
325                 330                 335                 340 agg ggt aga gct aag acc atg gct cta gtt gac atc cag ttg gat cac      1293
Arg Gly Arg Ala Lys Thr Met Ala Leu Val Asp Ile Gln Leu Asp His
            345                 350                 355 cat gaa cga tgc gat tgt atc tgc agc tca aga cca cct cga taa          1338
His Glu Arg Cys Asp Cys Ile Cys Ser Ser Arg Pro Pro Arg *
        360                 365                 370 gagaatgtgc acatccttac attaagcctg aaagaacctt tagtttaagg agggtgagat    1398
aagagaccct tttcctacca gcaaccaaac ttactactag cctgcaatgc aatgaacaca    1458
agtggttgct gagtctcagc cttgctttgt taatgccatg gcaagtagaa aggtatatca    1518
tcaacttcta tacctaagaa ataggattg catttaataa tagtgtttga ggttatatat     1578
```



```
tcaacttcta tacctaagaa ataggattg catttaataa tagtgtttga ggttatatat     1578
gcacaaacac acacagaaat atattcatgt ctatgtgtat atagatcaaa tgttttttt     1638
ttttggtata tataaccagg tacaccagag gttacatatg tttgagttag actcttaaaa    1698
tcctttgcca aaataaggga tggtcaaata tatgaaacat gtctttagaa aatttaggag    1758
ataaatttat ttttaaattt tgaaacacga aacaattttg aatcttgctc tcttaaagaa    1818
agcatcttgt atattaaaaa tcaaaagatg aggctttctt acatatacat cttagttgat    1878
tatt                                                                  1882
```

<210> SEQ ID NO 2
<211> LENGTH: 370
<212> TYPE: PRT
<213> ORGANISM: Homo sapiens

<400> SEQUENCE: 2

```
Met His Arg Leu Ile Phe Val Tyr Thr Leu Ile Cys Ala Asn Phe Cys
1               5                   10                  15

Ser Cys Arg Asp Thr Ser Ala Thr Pro Gln Ser Ala Ser Ile Lys Ala
            20                  25                  30

Leu Arg Asn Ala Asn Leu Arg Arg Asp Glu Ser Asn His Leu Thr Asp
        35                  40                  45

Leu Tyr Arg Arg Asp Glu Thr Ile Gln Val Lys Gly Asn Gly Tyr Val
    50                  55                  60

Gln Ser Pro Arg Phe Pro Asn Ser Tyr Pro Arg Asn Leu Leu Leu Thr
65                  70                  75                  80

Trp Arg Leu His Ser Gln Glu Asn Thr Arg Ile Gln Leu Val Phe Asp
                85                  90                  95

Asn Gln Phe Gly Leu Glu Glu Ala Glu Asn Asp Ile Cys Arg Tyr Asp
            100                 105                 110

Phe Val Glu Val Glu Asp Ile Ser Glu Thr Ser Thr Ile Ile Arg Gly
        115                 120                 125

Arg Trp Cys Gly His Lys Glu Val Pro Pro Arg Ile Lys Ser Arg Thr
    130                 135                 140

Asn Gln Ile Lys Ile Thr Phe Lys Ser Asp Asp Tyr Phe Val Ala Lys
145                 150                 155                 160
```

-continued

```
        Pro Gly Phe Lys Ile Tyr Tyr Ser Leu Leu Glu Asp Phe Gln Pro Ala
                    165                 170                 175

Ala Ala Ser Glu Thr Asn Trp Glu Ser Val Thr Ser Ile Ser Gly
                180                 185                 190

Val Ser Tyr Asn Ser Pro Ser Val Thr Asp Pro Thr Leu Ile Ala Asp
                    195                 200                 205

Ala Leu Asp Lys Lys Ile Ala Glu Phe Asp Thr Val Glu Asp Leu Leu
            210                 215                 220

Lys Tyr Phe Asn Pro Glu Ser Trp Gln Glu Asp Leu Glu Asn Met Tyr
        225                 230                 235                 240

Leu Asp Thr Pro Arg Tyr Arg Gly Arg Ser Tyr His Asp Arg Lys Ser
                        245                 250                 255

Lys Val Asp Leu Asp Arg Leu Asn Asp Asp Ala Lys Tyr Ser Cys
                    260                 265                 270

Thr Pro Arg Asn Tyr Ser Val Asn Ile Arg Glu Glu Leu Lys Leu Ala
                        275                 280                 285

Asn Val Val Phe Phe Pro Arg Cys Leu Leu Val Gln Arg Cys Gly Gly
            290                 295                 300

Asn Cys Gly Cys Gly Thr Val Asn Trp Arg Ser Cys Thr Cys Asn Ser
        305                 310                 315                 320

Gly Lys Thr Val Lys Lys Tyr His Glu Val Leu Gln Phe Glu Pro Gly
                        325                 330                 335

His Ile Lys Arg Arg Gly Arg Ala Lys Thr Met Ala Leu Val Asp Ile
                    340                 345                 350

Gln Leu Asp His His Glu Arg Cys Asp Cys Ile Cys Ser Ser Arg Pro
                355                 360                 365

Pro Arg
            370

<210> SEQ ID NO 3
<211> LENGTH: 1472
<212> TYPE: DNA
<213> ORGANISM: Mus musculus
<220> FEATURE:
<221> NAME/KEY: CDS
<222> LOCATION: (93)...(1205)

<400> SEQUENCE: 3
agggactgtg cagtagaaat ccgccgactc aacccttttgg gctttatttta tttacttttg     60 gagcaacgcg atccctaggt cgctgagccc aa atg caa cgg ctc gtt tta gtc       113
                                    Met Gln Arg Leu Val Leu Val
                                     1               5 tcc att ctc ctg tgc gcg aac ttt agc tgc tat ccg gac act ttt gcg      161
Ser Ile Leu Leu Cys Ala Asn Phe Ser Cys Tyr Pro Asp Thr Phe Ala
         10                  15                  20 act ccg cag aga gca tcc atc aaa gct ttg cgc aat gcc aac ctc agg      209
Thr Pro Gln Arg Ala Ser Ile Lys Ala Leu Arg Asn Ala Asn Leu Arg
     25                  30                  35 aga gat gag agc aat cac ctc aca gac ttg tac cag aga gag gag aac      257
Arg Asp Glu Ser Asn His Leu Thr Asp Leu Tyr Gln Arg Glu Glu Asn
 40                  45                  50                  55 att cag gtg aca agc aat ggc cat gtg cag agt cct cgc ttc ccg aac      305
Ile Gln Val Thr Ser Asn Gly His Val Gln Ser Pro Arg Phe Pro Asn
                 60                  65                  70 agc tac cca agg aac ctg ctt ctg aca tgg tgg ctc cgt tcc cag gag      353
Ser Tyr Pro Arg Asn Leu Leu Leu Thr Trp Trp Leu Arg Ser Gln Glu
             75                  80                  85
```

```
aaa aca cgg ata caa ctg tcc ttt gac cat caa ttc gga cta gag gaa    401
Lys Thr Arg Ile Gln Leu Ser Phe Asp His Gln Phe Gly Leu Glu Glu
         90                  95                 100 gca gaa aat gac att tgt agg tat gac ttt gtg gaa gtt gaa gaa gtc    449
Ala Glu Asn Asp Ile Cys Arg Tyr Asp Phe Val Glu Val Glu Glu Val
105                 110                 115 tca gag agc agc act gtt gtc aga gga aga tgg tgt ggc cac aag gag    497
Ser Glu Ser Ser Thr Val Val Arg Gly Arg Trp Cys Gly His Lys Glu
120                 125                 130                 135 atc cct cca agg ata acg tca aga aca aac cag att aaa atc aca ttt    545
Ile Pro Pro Arg Ile Thr Ser Arg Thr Asn Gln Ile Lys Ile Thr Phe
                140                 145                 150 aag tct gat gac tac ttt gtg gca aaa cct gga ttc aag att tat tat    593
Lys Ser Asp Asp Tyr Phe Val Ala Lys Pro Gly Phe Lys Ile Tyr Tyr
                155                 160                 165 tca ttt gtg gaa gat ttc caa ccg gaa gca gcc tca gag acc aac tgg    641
Ser Phe Val Glu Asp Phe Gln Pro Glu Ala Ala Ser Glu Thr Asn Trp
            170                 175                 180 gaa tca gtc aca agc tct ttc tct ggg gtg tcc tat cac tct cca tca    689
Glu Ser Val Thr Ser Ser Phe Ser Gly Val Ser Tyr His Ser Pro Ser
185                 190                 195 ata acg gac ccc act ctc act gct gat gcc ctg gac aaa act gtc gca    737
Ile Thr Asp Pro Thr Leu Thr Ala Asp Ala Leu Asp Lys Thr Val Ala
200                 205                 210                 215 gaa ttc gat acc gtg gaa gat cta ctt aag cac ttc aat cca gtg tct    785
Glu Phe Asp Thr Val Glu Asp Leu Leu Lys His Phe Asn Pro Val Ser
                220                 225                 230 tgg caa gat gat ctg gag aat ttg tat ctg gac acc cct cat tat aga    833
Trp Gln Asp Asp Leu Glu Asn Leu Tyr Leu Asp Thr Pro His Tyr Arg
                235                 240                 245 ggc agg tca tac cat gat cgg aag tcc aaa gtg gac ctg gac agg ctc    881
Gly Arg Ser Tyr His Asp Arg Lys Ser Lys Val Asp Leu Asp Arg Leu
                250                 255                 260 aat gat gat gtc aag cgt tac agt tgc act ccc agg aat cac tct gtg    929
Asn Asp Asp Val Lys Arg Tyr Ser Cys Thr Pro Arg Asn His Ser Val
265                 270                 275 aac ctc agg gag gag ctg aag ctg acc aat gca gtc ttc ttc cca cga    977
Asn Leu Arg Glu Glu Leu Lys Leu Thr Asn Ala Val Phe Phe Pro Arg
280                 285                 290                 295 tgc ctc ctc gtg cag cgc tgt ggt ggc aac tgt ggt tgc gga act gtc    1025
Cys Leu Leu Val Gln Arg Cys Gly Gly Asn Cys Gly Cys Gly Thr Val
                300                 305                 310 aac tgg aag tcc tgc aca tgc agc tca ggg aag aca gtg aag aag tat    1073
Asn Trp Lys Ser Cys Thr Cys Ser Ser Gly Lys Thr Val Lys Lys Tyr
            315                 320                 325 cat gag gta ttg aag ttt gag cct gga cat ttc aag aga agg ggc aaa    1121
His Glu Val Leu Lys Phe Glu Pro Gly His Phe Lys Arg Arg Gly Lys
            330                 335                 340 gct aag aat atg gct ctt gtt gat atc cag ctg gat cat cat gag cga    1169
Ala Lys Asn Met Ala Leu Val Asp Ile Gln Leu Asp His His Glu Arg
        345                 350                 355 tgt gac tgt atc tgc agc tca aga cca cct cga taa aacactatc         1215
Cys Asp Cys Ile Cys Ser Ser Arg Pro Pro Arg  *
360                 365                 370 acatctgtac tttgattatg aaaggacctt taggttacaa aaaccctaag aagcttctaa  1275
tctcagtgca atgaatgcat atggaaatgt tgctttgtta gtgccatggc aagaagaagc  1335
aaatatcatt aatttctata tacataaaca taggaattca cttatcaata gtatgtgaag  1395
atatgtatat atacttatat acatgactag ctctatgtat gtaaatagat taaatacttt  1455
```
attcagtata tttactg                                                    1472

<210> SEQ ID NO 4
<211> LENGTH: 370
<212> TYPE: PRT
<213> ORGANISM: Mus musculus

<400> SEQUENCE: 4

Met Gln Arg Leu Val Leu Val Ser Ile Leu Leu Cys Ala Asn Phe Ser
 1               5                  10                  15

Cys Tyr Pro Asp Thr Phe Ala Thr Pro Gln Arg Ala Ser Ile Lys Ala
            20                  25                  30

Leu Arg Asn Ala Asn Leu Arg Arg Asp Glu Ser Asn His Leu Thr Asp
        35                  40                  45

Leu Tyr Gln Arg Glu Glu Asn Ile Gln Val Thr Ser Asn Gly His Val
    50                  55                  60

Gln Ser Pro Arg Phe Pro Asn Ser Tyr Pro Arg Asn Leu Leu Leu Thr
65                  70                  75                  80

Trp Trp Leu Arg Ser Gln Glu Lys Thr Arg Ile Gln Leu Ser Phe Asp
                85                  90                  95

His Gln Phe Gly Leu Glu Glu Ala Glu Asn Asp Ile Cys Arg Tyr Asp
            100                 105                 110

Phe Val Glu Val Glu Val Ser Glu Ser Thr Val Val Arg Gly
        115                 120                 125

Arg Trp Cys Gly His Lys Glu Ile Pro Pro Arg Ile Thr Ser Arg Thr
    130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Phe Val Glu Asp Phe Gln Pro Glu
                165                 170                 175

Ala Ala Ser Glu Thr Asn Trp Glu Ser Val Thr Ser Ser Phe Ser Gly
            180                 185                 190

Val Ser Tyr His Ser Pro Ser Ile Thr Asp Pro Thr Leu Thr Ala Asp
        195                 200                 205

Ala Leu Asp Lys Thr Val Ala Glu Phe Asp Thr Val Glu Asp Leu Leu
    210                 215                 220

Lys His Phe Asn Pro Val Ser Trp Gln Asp Leu Glu Asn Leu Tyr
225                 230                 235                 240

Leu Asp Thr Pro His Tyr Arg Gly Arg Ser Tyr His Asp Arg Lys Ser
                245                 250                 255

Lys Val Asp Leu Asp Arg Leu Asn Asp Asp Val Lys Arg Tyr Ser Cys
            260                 265                 270

Thr Pro Arg Asn His Ser Val Asn Leu Arg Glu Glu Leu Lys Leu Thr
        275                 280                 285

Asn Ala Val Phe Phe Pro Arg Cys Leu Leu Val Gln Arg Cys Gly Gly
    290                 295                 300

Asn Cys Gly Cys Gly Thr Val Asn Trp Lys Ser Cys Thr Cys Ser Ser
305                 310                 315                 320

Gly Lys Thr Val Lys Lys Tyr His Glu Val Leu Lys Phe Glu Pro Gly
                325                 330                 335

His Phe Lys Arg Arg Gly Lys Ala Lys Asn Met Ala Leu Val Asp Ile
            340                 345                 350

Gln Leu Asp His His Glu Arg Cys Asp Cys Ile Cys Ser Ser Arg Pro
        355                 360                 365

-continued

Pro Arg
    370

<210> SEQ ID NO 5
<211> LENGTH: 24
<212> TYPE: DNA
<213> ORGANISM: Artificial Sequence
<220> FEATURE:
<223> OTHER INFORMATION: oligonucleotide primer ZC21,987

<400> SEQUENCE: 5
caacctgttg tttgtcccgt cacc                                          24

<210> SEQ ID NO 6
<211> LENGTH: 24
<212> TYPE: DNA
<213> ORGANISM: Artificial Sequence
<220> FEATURE:
<223> OTHER INFORMATION: oligonucleotide primer ZC21,120

<400> SEQUENCE: 6
tccagagcat ccgcaatcag agtg                                          24

<210> SEQ ID NO 7
<211> LENGTH: 25
<212> TYPE: DNA
<213> ORGANISM: Artificial Sequence
<220> FEATURE:
<223> OTHER INFORMATION: oligonucleotide primer ZC26317

<400> SEQUENCE: 7
atcacctcac agacttgtac cagag                                         25

<210> SEQ ID NO 8
<211> LENGTH: 25
<212> TYPE: DNA
<213> ORGANISM: Artificial Sequence
<220> FEATURE:
<223> OTHER INFORMATION: oligonucleotide primer ZC26318

<400> SEQUENCE: 8
cctacaaatg tcattttctg cttcc                                         25

<210> SEQ ID NO 9
<211> LENGTH: 6
<212> TYPE: PRT
<213> ORGANISM: Artificial Sequence
<220> FEATURE:
<223> OTHER INFORMATION: peptide

<400> SEQUENCE: 9

Glu Tyr Met Pro Met Glu
 1               5

<210> SEQ ID NO 10
<211> LENGTH: 6
<212> TYPE: PRT
<213> ORGANISM: Artificial Sequence
<220> FEATURE:
<223> OTHER INFORMATION: peptide

<400> SEQUENCE: 10

Glu Tyr Met Pro Thr Asp
 1               5